United States Patent [19]
Aoki et al.

[11] Patent Number: 4,880,869
[45] Date of Patent: Nov. 14, 1989

[54] β-AMINO-β-PROPIOLACTAM DERIVATIVE AND MOISTURE CURABLE POLYURETHANE COMPOSITION THEREOF

[75] Inventors: Masaaki Aoki, Zushi; Mayumi Tani, Yokohama; Masayuki Kamiyama, Yokohama; Kiyotsugu Asai, Yokohama, all of Japan

[73] Assignee: Mitsui Toatsu Chemicals, Inc., Tokyo, Japan

[21] Appl. No.: 251,376

[22] PCT Filed: Jan. 21, 1988

[86] PCT No.: PCT/JP88/00040
§ 371 Date: Sep. 14, 1988
§ 102(e) Date: Sep. 14, 1988

[87] PCT Pub. No.: WO88/05431
PCT Pub. Date: Jul. 28, 1988

[30] Foreign Application Priority Data

Jan. 22, 1987 [JP] Japan ................................. 62-11233
Mar. 13, 1987 [JP] Japan ................................. 62-56936
Nov. 9, 1987 [JP] Japan ............................... 62-281088
Dec. 23, 1987 [JP] Japan ............................... 62-323822

[51] Int. Cl.$^4$ ............................................. C08L 75/04
[52] U.S. Cl. .................................... 524/773; 524/783; 524/786; 524/787; 524/788; 524/789; 528/59; 528/73; 548/952
[58] Field of Search ............... 524/773, 783, 786, 787, 524/788, 789; 528/59, 73; 548/952

[56] References Cited

U.S. PATENT DOCUMENTS 4,088,644  5/1978  Gold ................................... 548/952

Primary Examiner—Maurice J. Welsh
Attorney, Agent, or Firm—Burns, Doane, Swecker & Mathis

[57] ABSTRACT

This invention relates to β-amino-β-propiolactam derivativatives, moisture curable polyurethane compositions and their applications.

The products of this invention have excellent characteristics such as good storage stability, rapid curing with atmospheric moisture and freedom from foaming.

More particularly, condensed compounds are obtained by reacting specific secondary diamines such as piperazine and 1,3-(4,4'-dipiperidyl)propane with monoaldehyde having at least 3 carbon atoms, for example, isobutylaldehyde and β-phenylpropylaldehyde. The β-amino-β-propiolactam derivatives are prepared by reacting the condensed compounds with monoisocyanate such as phenyl isocyanate and equimolar reaction products of diisocyanate with lower monohydric alcohol.

In addition, the moisture curable polyurethane compositions contain said derivatives and polyisocyanate and/or polyurethane prepolymer having terminal isocyanato radicals. Moisture curable sealing materials, wall covering materials and water proof materials are provided by the addition of various auxiliary agents to said compositions according to the field of application.

26 Claims, 5 Drawing Sheets

β-AMINO-β-PROPIOLACTAM DERIVATIVE AND MOISTURE CURABLE POLYURETHANE COMPOSITION THEREOF

FIELD OF THE INVENTION

This invention relates to a novel β-amino-β-propiolactam derivative which forms two secondary amino radicals by hydrolysis. The compound which generates two secondary amino radicals in the same molecule as a result of hydrolysis can be used for the curing agent of epoxy resin or polyurethane resin.

In addition, the present invention relates to a moisture curable polyurethane composition utilizing a reaction which forms two secondary amino radicals by hydrolyzing the novel β-amino-β-propiolactam derivative with atmospheric moisture.

Furthermore this invention relates to a sealing material, wall covering material, water proof material, coating or adhesive of moisture curable polyurethane which is industrially useful for buildings, vehicles and the like.

BACKGROUND OF THE INVENTION

Polyurethane resin has remarkably been used in recent years for the sealing material, wall covering material, water proof material, coating or adhesive, because the polyurethane resin is excellent in various properties such as rubber elasticity, abrasion resistance, long service life etc.

The method for preparing the polyurethane resin is substantially classified into two groups, that is, one component method and two component method. In the one component method, terminal isocyanato radicals of polyurethane prepolymer cures by the atmospheric moisture. In the two component method, prepolymer containing principal component and polyol containing curing agent are mixed at the time of application to cause cure.

One component type polyurethane can be used by anybody because of its easiness in application method and has recently been attracted much attention in particular.

The one component type polyurethane is referred to as so called moisture curable polyurethane and the following compositions are already known in the art.

(1) Moisture curable polyurethane compositions by use of a reaction of polyisocyanate with moisture (water), that is, a reaction wherein a part of isocyanate converts to amine by the decarboxylation of isocyanate/water adduct and resultant amine reacts with another polyisocyanate molecule to carry out curing.

(2) Moisture curable polyurethane compositions composed of polyketimine and polyisocyanate (British Patent 1064841).

(3) Moisture curable polyurethane compositions composed of polyenamine and polyisocyanate (TOKKAI-SHO 57-16126 (1982)).

The compositions(1), however, have a relatively good storage stability in a sealed vessel whereas they have a markedly poor curing ability and a disadvantage of foaming. Amine or tin catalysts may be incorporated in order to improve the curing ability. These additives, however, have an adverse effect on the storage stability of the compositions, accelerate foaming and cause problems in actual use.

The compositions(2) are required to block the isocyanato radical in order to employ as the moisture curable polyurethane compositions, because polyketimine reacts with polyisocyanate. Besides the system consisting of blocked polyisocyanate and polyketimine has a characteristic of non-foaming whereas the system has a very low curing rate and causes troubles in actual application.

In the compositions(3), polyenamine also reacts with polyisocyanate. Therefore the same as in polyketimine, isocyanato radicals should be blocked when aromatic isocyanate is used as polyisocyanate, and lead to troubles in practical use. It has been known that polyenamine can be applied to sealing materials etc. in combination with polyisocyanate having relatively low activity, for example, aliphatic or alicyclic polyisocyanate. This system has characteristics of non-foaming and rapid cure. Polyenamine, however, reacts very gradually with aliphatic or alicyclic polyisocyanate and leads to poor stability in a long storage period or even in completely sealed containers at somewhat elevated temperatures. As a result, the initial physical properties of the sealing material cannot be maintained, the viscosity of the material is remarkably increased and causes a disadvantage of very poor workability. Therefore any of known prior arts has been unsatisfactory.

The above mentioned various problems are required to overcome industrially. That is, very important properties of such types of polyurethane are good storage stability in the sealed containers, high retention of the initial physical properties, prevention of gelation and good stability in viscosity. Curing rate must also be quick without foaming under atmospheric moisture. The value of commodity depends upon these properties.

In other words, a moisture curable polyurethane composition is strongly desired which is excellent in storage stability, capable of being stored for a long period under constant viscosity and also rapidly cured without foaming in the presence of moisture.

DISCLOSURE OF THE INVENTION

The present inventors have extensively investigated to overcome aforesaid problems. Consequently they have developed a novel β-amino-β-propiolactam derivative which forms two secondary amino radicals in the same molecule as a result of hydrolysis. Thus the present invention has been completed.

In addition, the moisture curable polyurethane composition which is excellent in storage stability and capable of being rapidly cured under atmospheric moisture has been obtained by applying the β-amino-β-propiolactam derivative of this invention. The polyurethane composition has further developed various uses.

That is, an invention of the present invention is a β-amino-β-propiolactam derivative having the formula (I)

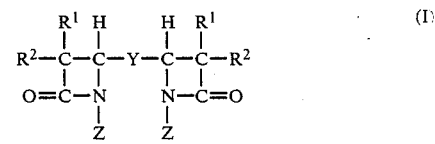

wherein $R^1$ is a monovalent radical selected from the group consisting of a hydrogen atom, alkyl radical having 1–8 carbon atoms and cycloalkyl radical; $R^2$ is a monovalent radical selected from the group consisting of an alkyl radical having 1–12 carbon atoms and cycloalkyl radical; Y is a divalent radical obtained by eliminating a hydrogen atom respectively from each secondary amino group in an aliphatic or alicyclic di-secondary-amine having 1 –22 carbon atoms; and Z is a monovalent radical obtained by eliminating an isocyanato radical from aliphatic or aromatic monoisocyanate.

Another invention of the present invention is a moisture curable polyurethane composition containing the β-amino-β-propiolactam derivative and a polyisocyanate and/or a polyurethane prepolymer having a terminal isocyanato radical.

Further invention of the present invention is a sealing material or a wall covering material of moisture curable polyurethane containing the β-amino-β-propiolactam derivative, the polyisocyanate and/or the polyurethane prepolymer having the terminal isocyanato radical and a thixotropic agent.

Still another invention of the present invention is a water proof material of moisture curable polyurethane containing the β-amino-β-propiolactam derivative, the polyisocyanate and/or the polyurethane prepolymer having the terminal isocyanato radical and a filler.

The practical method of this invention will be described below.

The β-amino-β-propiolactam derivative of this invention is prepared by the following process.

Aliphatic or alicyclic diamine having two secondary amino radicals (hereinafter diamine having two secondary amino radicals abbreviate to di-secondary-amine) is first of all reacted with aldehyde to form dienamine. The resulting dienamine is then reacted with aliphatic or aromatic isocyanate to obtain the β-amino-β-propiolactam derivative having the aforesaid formula (I).

The di-secondary-amine which is used for preparing the
β-aminoβ-propiolactam derivative of this invention is the aliphatic or alicyclic diamine of branched, linear or cyclic type having 1 –22 carbon atoms. Examples of di-secondary-amine which are particularly preferred in the present invention are aliphatic and alicyclic di-secondary-amine derivatives having the following formula (II), (III) or (IV).

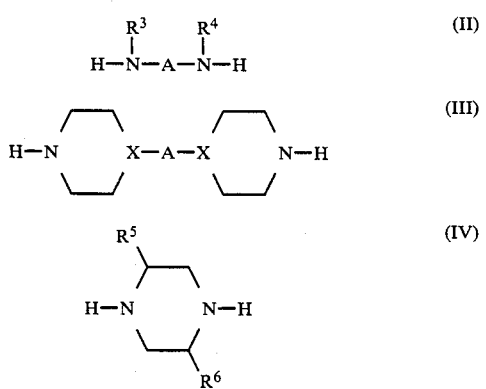

wherein $R^3$ and $R^4$ are respectively a monovalent radical selected from the group consisting of an alkyl radical of 1 –8 carbon atoms, cycloalkyl radical and aryl radical; $R^5$ and $R^6$ are respectively a monovalent radical selected from the group consisting of a hydrogen atom, alkyl radical of 1 –6 carbon atoms and a cycloalkyl radical; X is a CH radical or a nitrogen atom; A is a divalent radical selected from the group consisting of an alkylene radical of 1 –10 carbon atoms, cycloalkylene radical and arylene radical; and A includes a bond when X is a CH radical.

The di-secondary-amine of the above formula (II) which is suitably be used in this invention includes, for example, N,N′-dimethylethylenediamine, N,N′-diethylethylenediamine, N,N′-dicyclohexylethylenediamine, N,N′-diphenylethylenediamine, N,N′-dimethyl-1,4-diaminocyclohexane, N,N′-dimethyl-p-phenylenediamine and N,N′-diisobutyl-2,2,4-trimethylhexamethylenediamine.

The di-secondary-amine of the above formula (III) includes, for example, 1,3-(4,4′-dipiperidyl)propane, 1,2-(4,4′-dipiperidyl)ethane, 4,4′-dipiperidyl, 1,3-(4,4′-dipiperazyl)propane and N,N′-dipiperazylmethane.

The di-secondary-amine of the above formula (IV) includes, for example, piperazine, 2-methylpiperazine, 2,5-dimethylpiperazine and 2-cyclohexylpiperazine.

The aldehyde compound which is reacted with aforesaid di-secondary-amine is aldehyde having the following formula:

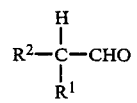

wherein $R^1$ and $R^2$ is the same as in above formula (I).

The aldehyde which is used in this invention includes, for example, propionaldehyde, n-butylaldehyde, isobutylaldehyde, diethylacetaldehyde, 2-ethylhexanal, 3-methylbutanal, 2-methylpentanal, 11-methyldodecanal and 2-phenylpropanal.

The isocyanate which is employed in this invention is aliphatic or aromatic isocyanate and includes, for example, monoisocyanate such as phenyl isocyanate, o-tolyl isocyanate, p-tolyl isocyanate, methyl isocyanate and butyl isocyanate.

The isocyanate derived from diisocyanate can also be used in this invention. The diisocyanate includes, for example, tolylene diisocyanate including various isomers and mixtures thereof (hereinafter referred to as TDI), diphenylmethane diisocyanate including various mixtures of isomers (hereinafter referred to as MDI), 3,3′-dimethyl-4,4′-biphenylene diisocyanate, 1,4-phenylene diisocyanate, m-xylylene diisocyanate (hereinafter referred to as XDI), tetramethylxylylene diisocyanate, hexamethylene diisocyanate, dicyclohexylmethane diisocyanate, isophorone diisocyanate, hydrogenated xylylene diisocyanate, 1,4-diisocyanatocyclohexane, 2,4-diisocyanato-1-methylcyclohexane, and 1,6-diisocyanato-2,4,4-trimethylcyclohexane. The above mentioned diisocyanate is reacted with compounds having active hydrogen such as secondary amines or alcohols. The resulting monoisocyanate having the following formula (V) or (VI) is used in the process of this invention.

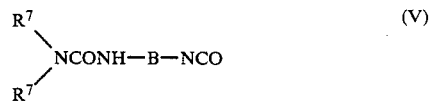

wherein $R^7$ is an alkyl radical of 1 –10 carbon atoms and $R^8$ is an alkyl radical of 1–10 carbon atoms or an alkoxy(polyethyleneoxy)alkyl radical.

The β-amino-β-propiolactam derivative of this invention is prepared by conducting the azeotropic dehydration reaction of the aforesaid di-secondary-amine with above mentioned aldehyde in the presence of solvent such as toluene or xylene. The raction is continued until the termination of water distillation into the water separator. The condensed compound thus obtained has the following formula (VII):

$$R^1-\underset{\underset{H}{|}}{\overset{\overset{R^2}{|}}{C}}=\underset{}{\overset{H}{C}}-Y-\underset{}{\overset{H}{C}}=\underset{\underset{H}{|}}{\overset{\overset{R^2}{|}}{C}}-R^1 \quad (VII)$$

wherein $R^1$, $R^2$ and Y are the same as in above formula (I). In the next step, above described isocyanate is reacted with the resulting condensed compound by adding dropwise under stirring to obtain the β-aminoβ-propiolactam derivative. That is, the condensed compound is dissolved in the solvent and added dropwise with isocyanate under stirring with care to prevent violent temperature rise of the solution.

The temperature during the reaction is 20°–100° C. and preferably 30°–80° C. The reaction time is 3–300 hours and preferably 5–150 hours.

The ratio of isocyanate to the condensed compound (VII) is 0.5–1.5 equivalents, preferably 0.7–1.3 equivalents of isocyanate radical per equivalent of double bond in the condensed compound (VII).

The β-amino-β-propiolactam derivative of the resulting condensed compound is illustrated by the formula (I). Besides the derivative of the formula (I), a polymer having the following formula (VIII) and a compound formed by the addition of isocyanate to only one of the two double bonds in the resulting condensed compound (VII) are also found as by-products.

The mixture of these adducts may also be used in the method of this invention and the invention is not restricted to the derivative having the formula (I).

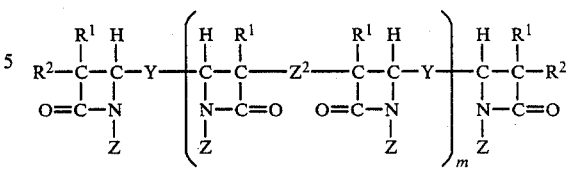

wherein $R^1$, $R^2$, Y and Z are the same as in above formula (I); Z2 is a divalent radical obtained by eliminating two isocyanato radicals from a diisocyanate compound; and m is an integer of 1–5.

Among the various raw materials mentioned above, the di-secondary-amine which is particularly suitable for carrying out the invention includes 4,4'-dipiperidylpropane, piperazine, N,N'-dimethylethylenediamine and 2-methylpiperazine. Besides suitable aldehyde is isobutyl aldehyde.

Isocyanate which is suitable for the addition reaction with the condensed compound (VII) of the di-secondary-amine and aldehyde includes the following isocyanates:

o-Tolyl isocyanate.

m-Isopropoxycarbonylamino-o- or p-tolyl isocyanate obtained by reacting equimolar amounts of TDI and isopropyl alcohol to form urethane linkage.

3-(1-Methylpropoxycarbonylaminomethyl)benzyl isocyanate obtained by reacting equimolar amounts of XDI and 1-methylpropanol to form urethane linkage.

6-(2-Ethylhexyloxycarbonylamino)hexyl isocyanate obtained by reacting equimolar amounts of hexamethylene diisocyanate and 2-ethylhexanol to form urethane linkage.

Table-1 illustrates preferred combinations of radicals $R^1$, $R^2$, Y and Z in the formula (I) for the practice of this invention, when the β-amino-β-propiolactam derivative (hereinafter abbreviated as LAC) is prepared by the addition of isocyanate to the condensed compound (VII) of di-secondary-amine and aldehyde.

$$R^2-\underset{\underset{O=C-N}{|}}{\overset{\overset{R^1}{|}}{C}}-\underset{H}{\overset{H}{C}}-Y-\underset{H}{\overset{H}{C}}-\underset{\underset{N-C=O}{|}}{\overset{\overset{R^1}{|}}{C}}-R^2$$

| LAC | $R_1$ | $R_2$ | Y | Z |
|---|---|---|---|---|
| 1 | CH$_3$ | CH$_3$ | 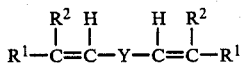 | phenyl |
| 2 | " | " | " | (CH$_3$)$_2$CHOC(O)NH–C$_6$H$_3$(CH$_3$)–* |
| 3 | " | " | " | (C$_2$H$_5$)(CH$_3$)CHOC(O)NHCH$_2$–C$_6$H$_4$–CH$_2$– |

-continued structure:
$$R^2-\underset{O=C-N}{\underset{|}{\overset{R^1}{\underset{|}{C}}}-\underset{|}{\overset{H}{C}}}-Y-\underset{N-C=O}{\underset{|}{\overset{H}{C}}-\underset{|}{\overset{R^1}{C}}}-R^2$$
(with Z on each N)

| LAC | R₁ | R₂ | Y | Z |
|---|---|---|---|---|
| 4 | " | " | " | C₂H₅(OC₂H₄)₂OC(=O)NHCH₂–C₆H₄–CH₂– |
| 5 | " | " | " | (C₄H₉)₂NC(=O)NHC₆H₁₂– |
| 6 | " | " | –N(piperidine)–(CH₂)₃–(piperidine)N– | –C₆H₃(CH₃)– |
| 7 | " | " | –N(CH₃)–C₂H₄–N(CH₃)– | (CH₃)₂CHOC(=O)NH–C₆H₃(CH₃)–CH₃* |
| 8 | " | " | –N(piperazine-2-CH₃)N– | (C₂H₅)(CH₃)CHOC(=O)NHCH₂–C₆H₄–CH₂– |
| 9 | " | " | –N(piperazine)N– | (C₂H₅)(C₄H₉)CHCH₂OC(=O)NHC₆H₁₂– |
| 10 | " | C₂H₅ | " | (CH₃)₂CHOC(=O)NH–C₆H₃(CH₃)–CH₃* |
| 11 | C₂H₅ | " | " | –C₆H₅ |
| 12 | CH₃ | | C₆H₅–(piperidine)N–(CH₂)₃–(piperidine)N– | –C₆H₅ |

*isomers contained

That is, LAC-1

1,4-bis(3,3-dimethyl-2-oxo-1-phenylazetidine-4-yl)piperazine. It is a lactam obtained by condensing 1 mole of piperazine with 2 moles of isobutylaldehyde and successively by the addition of 2 moles of phenyl isocyanate.

LAC-2 is 1,4-bis[3,3-dimethyl-2-oxo-1-(m-isopropoxycarbonylamino-o- or p-tolyl)azetidine-4-yl]piperazine. It is a lactam obtained by condensing 1 mole of piperazine with 2 moles of isobutylaldehyde and successively by the addition of 2 moles of reaction product derived from equimolar amounts of 2,4-TDI and isopropyl alcohol.

LAC-3 is 1,4-bis[3,3-dimethyl-2-oxo-1-(3-(1-methylpropoxycarbonylaminomethyl)- benzyl) azetidine-4-yl]piperazine. It is a lactam obtained by condensing 1 mole of piperazine with 2 moles of isobutylaldehyde and successively by the addition of 2 moles of reaction product derived from equimolar amounts of XDI and 1-methylpropanol.

LAC-4 is 1,4-bis[3-3-dimethyl-2-oxo-1-[3-(2-(2-ethoxyethoxy)ethoxycarbonylaminomethyl)benzyl]azetidine-4-yl]piperazine. It is a lactam obtained by condensing 1 mole of piperazine with 2 moles of isobutylaldehyde and successively by the addition of 2 moles of reaction product derived from equimolar amounts of XDI and 2-(2-ethoxyethoxy)ethanol.

LAC-5 is
1,4-bis[3,3-dimethyl-2-oxo-1-(3,3-dibutylureidohexyl)azetidine-4-yl]piperazine. It is a lactam obtained by condensing 1 mole of piperazine with 2 moles of isobutylaldehyde and successively by the addition of 2 moles of reaction product derived from equimolar amounts of hexamethylene diisocyanate and dibutylamine.

LAC-6 is
1,3-bis[1-(3,3-dimethyl-2-oxo-1-o-tolylazetidine-4-yl)piperidine-4-yl]propane. It is a lactam obtained by condensing 1 mol of 1,3-(4,4'-dipiperidyl)propane with 2 moles of isobutylaldehyde and successively by the addition of 2 moles of o-tolyl isocyanate.

LAC-7 is
N,N'-bis[3,3-dimethyl-2-oxo-1-(m-isopropoxycarbonylamino-o- or p-tolyl)azetidine-4-yl]-N,N'-dimethylethylenediamine. It is a lactam obtained by condensing 1 mole of N,N'-dimethylethylenediamine with 2 moles of isobutylaldehyde and successively by the addition of 2 moles of reaction product derived from equimolar amounts of 2,4-TDI and isopropyl alcohol. LAC-8 is
1,4-bis[3,3-dimethyl-2-oxo-1-(3-(1-methylpropoxycarbonylaminomethyl)-benzyl)azetidine-4-yl]-2-methylpiperazine. It is a lactam obtained by condensing 1 mole of 2-methylpiperazine with 2 moles of isobutylaldehyde and successively by the addition of 2 moles of reaction product derived from equimolar amounts of XDI and 1-methylpropanol.

LAC-9 is
1,4-bis[3,3-dimethyl-2-oxo-1-(2-ethylhexyloxycarbonylaminohexyl)azetidine-4-yl]piperazine. It is a lactam obtained by condensing 1 mole of piperazine with 2 moles of isobutylaldehyde and successively by the addition of reaction product derived from equimolar amounts of hexamethylene diisocyanate and 2-ethylhexanol.

LAC-10 is
1,4-bis[3-methyl-3-ethyl-2-oxo-1-(m-isopropoxycarbonylamino-o- or p-tolyl)azetidine-4-yl]piperazine. It is a lactam obtained by condensing 1 mole of piperazine with 2 moles of 2-methylbutylaldehyde and successively by the addition of 2 moles of reaction product derived from equimolar amounts of TDI and isopropyl alcohol.

LAC-11 is
1,4-bis(3,3-diethyl-2-oxo-1-phenylazetidine-4-yl)piperazine. It is a lactam obtained by condensing 1 mole of piperazine with 2 moles of 2-ethylbutylaldehyde and successively by the addition of 2 moles of phenyl isocyanate.

LAC-12 is
1,3-bis[1-(3-methyl-3-phenyl-2-oxo-1-phenylazetidine-4-yl)piperidine-4-yl]propane. It is a lactam obtained by condensing 1 mole of 1,3-(4,4'-dipiperidyl)propane with 2 moles of 2-phenylpropylaldehyde and successively by the addition of 2 moles of phenyl isocyanate.

Polyisocyanate which is employed for the preparation of moisture curable polyurethane composition in this invention includes, for example, 2,4-TDI, 2,6-TDI and their mixtures, crude TDI, 4,4'-diphenylmethane diisocyanate, 2,4'-diphenylmethane diisocyanate and their mixtures, polymethylenepolyphenyl polyisocyanate (crude diphenylmethane diisocyanate), XDI, hexamethylene diisocyanate, dicyclohexylmethane diisocyanate, isophorone diisocyanate, hydrogenated xylylen diisocyanate, carbodiimide modified polyisocyanates and dimers and trimers of these polyisocyanates.

Polyurethane prepolymer having terminal isocyanato radicals which is used for preparing the moisture curable polyurethane composition of this invention can be obtained by reacting above mentioned polyisocyanate with below described polyol at 100° C for several hours. The isocyanato radical content of prepolymer is preferably in the range of 0.5–20% by weight and more preferably 1.5–15% by weight.

Polyol which is employed for the preparation of polyurethane prepolymer having terminal isocyanato radicals is polyetherpolyol obtained by conducting addition polymerization of alkylene oxide to polyhydric alcohol. Alkylene oxide includes, for example, ethylene oxide, propylene oxide and butylene oxide. Polyhydric alcohol includes, for example, ethylene glycol, propylene glycol, glycerol, trimethylolpropane and pentaerythritol. Alkylene oxide and polyhydric alcohol may be used singly or in combination of two and more.

Besides other types of polyol which can be used are polyester polyol obtained by reacting polycarboxylic acid with a low molecular weight polyol, polyester polyol obtained by polymerizing caprolactone and hydroxyl containing higher fatty acid esters such as castor oil. Other useful polyols are polymer polyol obtained by grafting ethylenically unsaturated compounds such as acrylonitrile, styrene, methyl methacrylate etc. on the aforesaid known polyether or polyester polyol, and 1,2- or 1,4-polybutadiene polyol and its hydrogenation product.

In addition, low molecular weight polyhydric alcohol may be added, if required, to the above mentioned polyol. Such polyhydric alcohol includes, for example, ethylene glycol, diethylene glycol, propylene glycol, tripropylene glycol, butanediol, hexanediol, glycerol, trimethylolpropane and hexanetriol.

The moisture curable polyurethane composition of this invention is useful as a raw-material of, for example, sealing materials, wall covering materials and water proof materials as well as coatings and adhesives.

That is, sealing materials and wall covering materials of the moisture curable polyurethane are provided by the addition of a thixotropic agent to the above mentioned moisture curable polyurethane composition which contains the β-amino-β-propiolactam derivative of this invention and polyisocyanate and/or polyurethane prepolymer having terminal isocyanato radicals.

The thixotropic agent which may be used in the composition of this invention includes, for example, colloidal silica, fatty acid amide wax, aluminum stearate, surface treated bentonite, polyethylene short fiber and phenolic resin short fiber. Colloidal silica and fatty acid amide wax are particularly preferred among the agent. The thixotropic agent is used singly or in combination of the two and more. The amount in use is in the range of 3–10% by weight of the composition.

Furthermore water proof material of the moisture curable polyurethane are provided by the addition of a filler to the above mentioned moisture curable polyurethane composition which contains the β-amino-β- propiolactam derivative of this invention and polyisocyanate and/or polyurethane prepolymer having terminal isocyanato radicals.

The filler which may be used in the composition of this invention includes, for example, calcium carbonate, titanium oxide, calcium hydroxide, calcium oxide, talc, clay, aluminum sulfate, kaolin, zeolite, diatomaceous earth, carbone black, polyvinyl chloride fine powder, glass balloom, phenolic resin balloon and polyvinyliden chloride balloon. Preferably used are calcium carbonate, titanium oxide, calcium hydroxide, calcium oxide, talc, clay, aluminum sulfate and polyvinyl chloride fine powder. The filler is used singly or in combination of the two and more. The amount in use is in the range of 5–50% by weight of the composition.

The moisture curable polyurethane composition of this invention may be added with plasticizer and other additives according to the field of application. The thixotropic agent and filler may also be added when needed.

The moisture curable sealing materials and wall covering materials may also be used with the addition of plasticizer, filler and other additives depending upon their use.

The moisture curable water proof materials of this invention may also be employed with the addition of plasticizer, thixotropic agent and other additives according to the field of application.

The plasticizer which may be used in this invention include, for example, dioctyl phthalate (DOP), dibutyl phthalate (DBP), dilauryl phthalate (DLP), butyl benzyl phthalate (BBP), dioctyl adipate (DOA), diisodecyl adipate (DIDA) and trioctyl phosphate (TOP). Plasticizers are used in the range of 1–50% by weight of the composition.

Other auxiliary agents which may optionally be used are solvents such as aromatic hydrocarbons, aliphatic hydrocarbons, petroleum based solvents, esters, ketones, ether esters etc.; adhesion assistants such as silane coupling agents, titanium coupling agents and aluminum coupling agents etc.; precipitation inhibitors; stabilizers; coloring agents such as pigments, dyestuffs etc.; antifoaming agents and the like.

In order to practice the present invention, fillers, plasticizers, thixotropic agents and other auxiliary agents are charged into a blender such as planetary mixer or dissolver and mixed. The resulting mixture is then added with polyisocyanate and/or polyurethane prepolymer having terminal isocyanato radicals and the β-amino-βpropiolactam derivative and thoroughly mixed.

When the moisture content of various additives is high, attention should be given to previously dry these additives or to preferably add dehydrating agents such as zeolite.

The resulting moisture curable polyurethane composition is packed and stored in a sealed can under nitrogen atmosphere.

The moisture cure polyurethane composition of this invention which contains a nevel β-amino-β-propiolactam derivative and polyisocyanate and/or polyurethane prepolymer having terminal isocyanato radicals has an excellent storage stability in a sealed container under conditions isolated from atmospheric moisture. The composition has a high retention of its physical properties and good stability of viscosity even stored at elevated temperatures. On the other hand, when the composition is once exposed to air, it rapidly solidifies and provides non-foamed polyurethane resin having excellent mechanical properties, which is quite different from conventional moisture curable polyurethanes.

THE BEST MODE OF OPERATION OF THE INVENTION

The method for preparing and applying the β-amino-β-propiolactam derivative and the moisture curable polyurethane composition of this invention will hereinafter be described in detail with respect to the following examples. In the examples, part means part by weight.

EXAMPLE 1

A reaction vessel fitted with a water separator was charged with 25 parts of piperazine and 83.7 parts of isobutylaldehyde and heated to reflux with stirring under introduction of nitrogen stream. A half of calculated amount of water was separated during 5 hours and theoretical amount of water was separated during 20 hours.

Excess isobutylaldehyde was distilled off and the residue was distilled under vacuum to obtain transparent liquid boiling at 62° C./0.1mmHg. The liquid was 1,4-bis(2-methyl-1-propenyl)piperazine and solidified on standing.

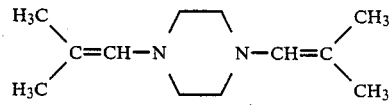

This compound was abbreviated as ENA-1. The results of elementary analysis were as follows.

| Elementary analysis ($C_{12}H_{22}N_2$) | | | |
|---|---|---|---|
| | C | H | N |
| Calculated (%) | 74.2 | 11.3 | 14.4 |
| Found (%) | 74.5 | 11.2 | 14.3 |

In the next step, a 1l reaction vessel was charged with 167 parts (0.86 mole) of ENA-1 and 167 parts of ethoxyethyl acetate. A dropping funnel was charged with 250 parts of phenyl isocyanate and fitted on the reaction vessel.

The mixture in the reaction vessel was stirred at room temperature and added dropwise with phenyl isocyanate over an hour under nitrogen atmosphere with care to prevent violent temperature rise of the mixture.

The reaction mixture was stirred for 2 hours after completing the dropwise addition and allowed to stand for 16 hours at the room temperature.

The IR absorption spectrum was examined on the mixture thus obtained. The characteristic absorption of NCO at 2300 cm$^-$ and that of <N—CH=C> at 1675 cm$^{-1}$ were disappeared. Thus the ethoxyethyl acetate solution of desired compound (LAC-ls) was obtained.

Figure 1:
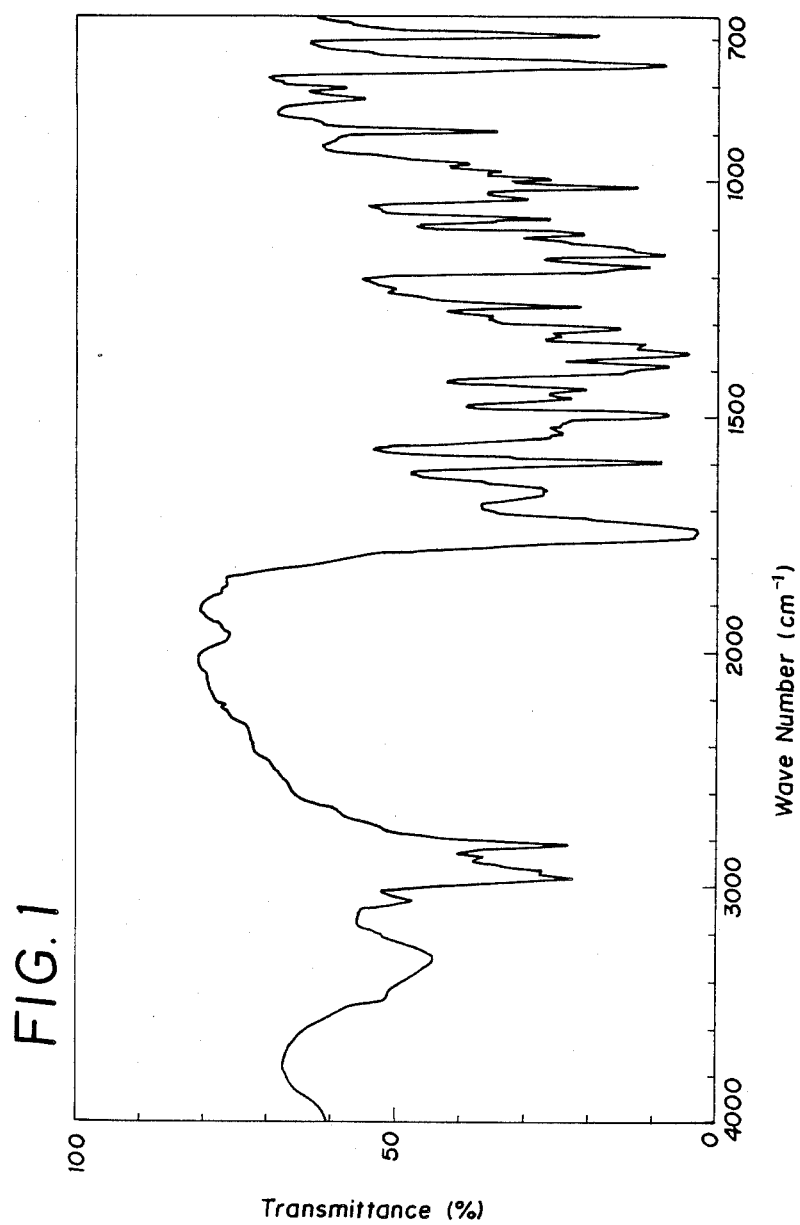
FIG. 1 to FIG. 5 illustrate examples of IR absorption spectra on the β-amino-β-propiolactam derivative in this invention.

Crystals were separated by mixing 10 parts of LAC-ls with 100 parts of anhydrous toluene. The crystals were filtered and dried under reduced pressure at 50° C. for 20 hours to obtain about 5 parts of 1,4-bis(3,3-dimethyl-2-oxo-1-phenylazetidine-4-yl)piperazine (LAC-1). Results of analysis on LAC-1 are illustrated in Table 2 and IR absorption spectrum is shown in FIG. 1.

EXAMPLE 2

A 2l reaction vessel was charged with 194 parts (1 mole) of ENA-1 obtained in Example 1 and 194 parts of ethoxyethyl acetate.

Separately 348 parts (2.0 moles) of 2,4-TDI, 120 parts (2.0 moles) of isopropyl alcohol and 247 parts of ethoxyethyl acetate were uniformly mixed and reacted at 80° C for 4 hours under nitrogen atmosphere to obtain a reaction product having an isocyanato radical content of 11.7% by weight.

The reaction product was charged into a dropping funnel and added dropwise into the above reaction vessel. The dropwise addition was conducted with stirring at the room temperature over an hour under nitrogen atmosphere with care to prevent violent temperature rise of the reaction mixture. After completing the addition, the reaction mixture was further stirred for 2 hours and allowed to stand for 16 hours at the room temperature.

Then IR absorption spectrum was examined on the mixture thus obtained. The characteristic absorption of NCO at 2300 cm$^{-1}$ and that of $<$N—CH=C$>$ at 1675 cm$^{-1}$ were disappeared and the ethoxyethyl acetate solution of desired compound (LAC-2s) was obtained.

Crystals were separated by mixing 10 parts of LAC-2s and 100 parts of anhydrous toluene. The crystals were filtered and dried under reduced pressure at 50° C. for 20 hours to obtain about 5 parts of 1,4-bis[3,3-dimethyl-2-oxo-1-(m-isopropoxycarbonylamino-o- or p-tolyl)azetidine-4-yl]piperazine (LAC-2).

Figure 2:
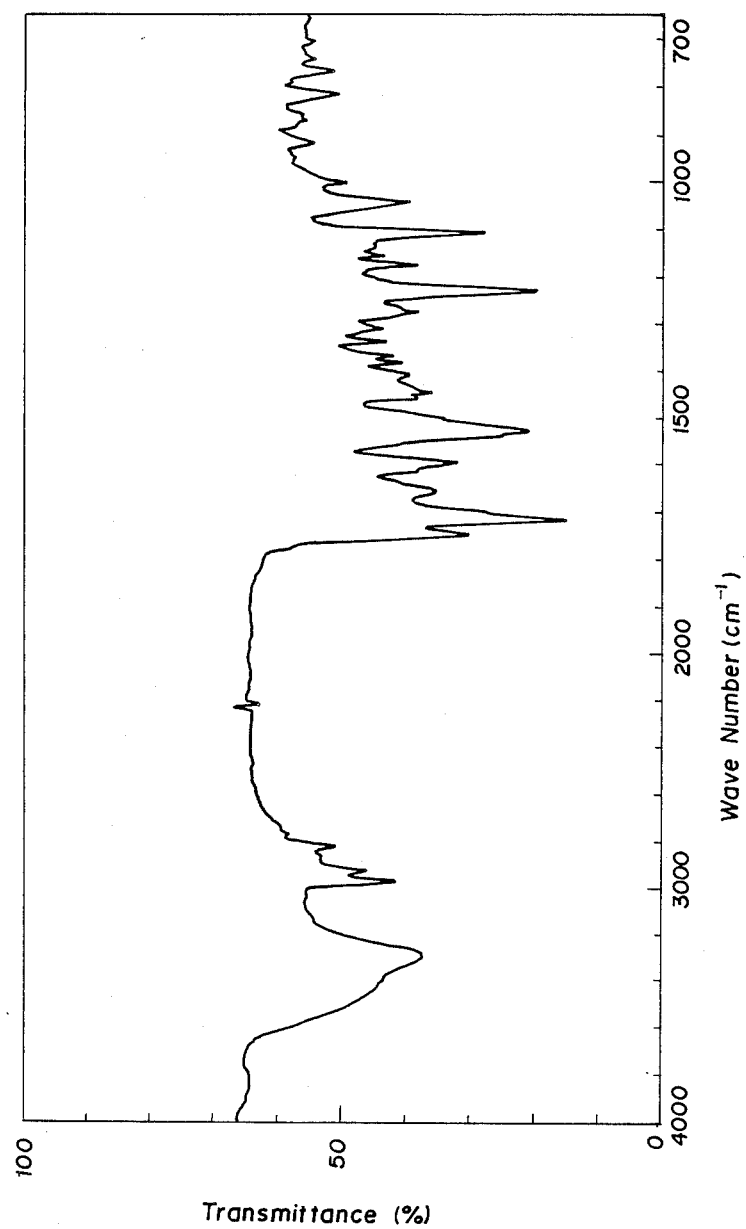

Results of analysis on LAC-2 are illustrated in Table 2 and IR absorption spectrum is shown in FIG. 2.

EXAMPLE 3

A 2l reaction vessel was charged with 194 parts (1 mole) of ENA-1 obtained in Example 1 and 194 parts of ethoxyethyl acetate.

Separately 376 parts (2.0 moles) of XDI, 148 parts (2.0 moles) of 1-methylpropanol and 276 parts of ethoxyethyl acetate were uniformly mixed and reacted at 80° C for 4 hours under nitrogen atmosphere to obtain a reaction product having an isocyanato radical content of 10.5% by weight.

The reaction product was charged into a dropping funnel and added dropwise into the above reaction vessel. The dropwise addition was conducted with stirring at the room temperature over an hour under nitrogen atmosphere with care to prevent violent temperature rise of the reaction mixture. After completing the addition, the reaction mixture was further reacted at 70° C for 100 hours under nitrogen atmosphere.

Then IR absorption spectrum was examined on the mixture thus obtained. The characteristic absorption of NCO at 2300 cm$^{-1}$ and that of $<$N—CH=C$>$ at 1675 cm$^{-1}$ were disappeared and the ethoxyethyl acetate solution of desired compound (LAC-3s) was obtained.

Crystals were separated by mixing 10 parts of LAC-3s and 100 parts of anhydrous toluene. The crystals were filtered and dried under reduced pressure at 50° C for 20 hours to obtain about 5 parts of 1,4-bis[3,3-dimethyl-2-oxo-1-(3-(1-methylpropoxycarbonylaminomethyl)-benzyl)azetidine-4-yl]piperazine (LAC-3).

Figure 3:
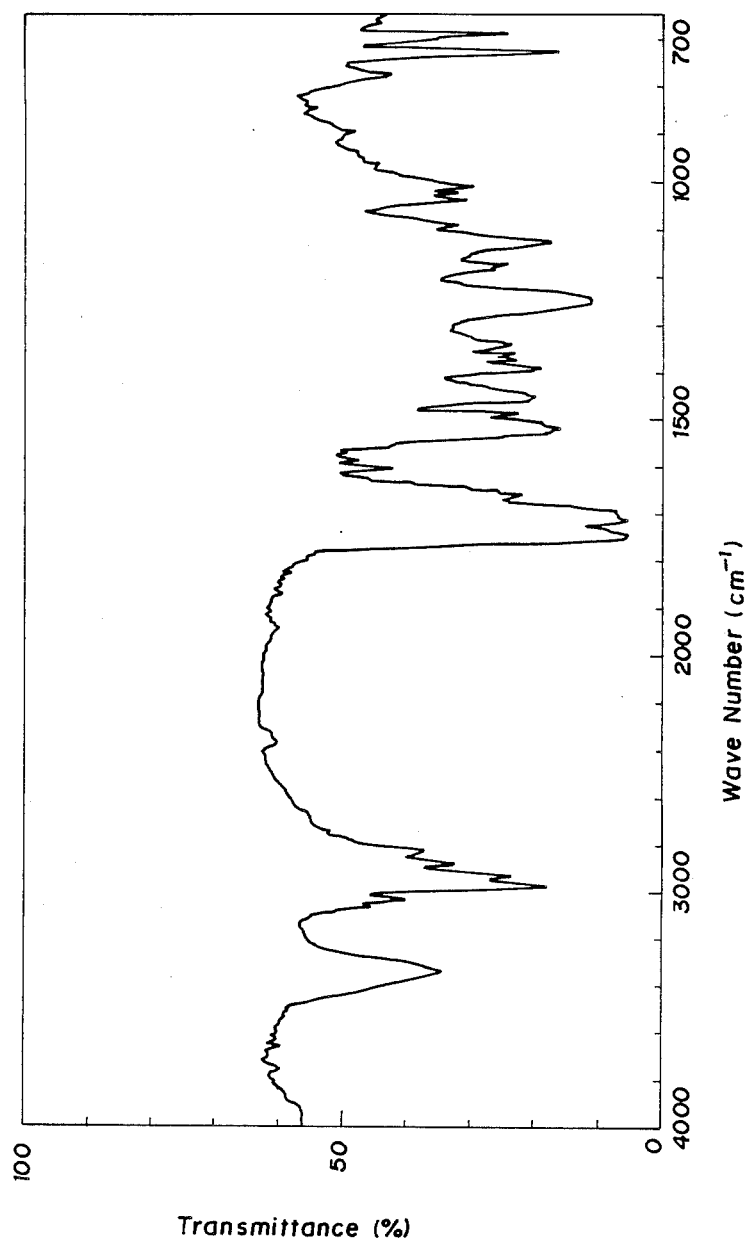

Analytical results on LAC-3 are illustrated in Table 2 and IR absorption spectrum is shown in FIG. 3.

EXAMPLE 4

A 2l reaction vessel was charged with 194 parts ( mole) of ENA-1 obtained in Example 1 and 194 parts of toluene.

Separately 376 parts (2.0 moles) of XDI, 268 parts (2.0 moles) of 2-(2-ethoxyethoxy)ethanol and 156 parts of toluene were uniformly mixed and reacted at 80° C for 4 hours under nitrogen atmosphere to obtain a reaction product having an isocyanato radical content of 10.5% by weight.

The reaction product was charged into a dropping funnel and added dropwise into the above reaction vessel. The dropwise addition was conducted with stirring at the room temperature over an hour under nitrogen atmosphere with care to prevent violent temperature rise of the reaction mixture. After completing the addition, the reaction mixture was further reacted at 70° C for 100 hours under nitrogen atmosphere.

Then IR absorption spectrum was examined on the mixture thus obtained. The characteristic absorption of NCO at 2300 cm$^{-1}$ and that of $<$N—CH=C$>$ at 1675 cm$^{-1}$ were disappeared and the toluene solution of desired product (LAC-4s) was obtained.

Solvent was removed from 10 parts of LAC-4s at 60° C. for 20 hours under reduced pressure to obtain about 5 parts of 1,4-bis[3,3-dimethyl-2-oxo-1-[3-(2-(2-ethoxyethoxy)ethoxycarbonylaminomethyl)benzyl]azetidine-4-yl]piperazine (LAC-4).

Figure 4:
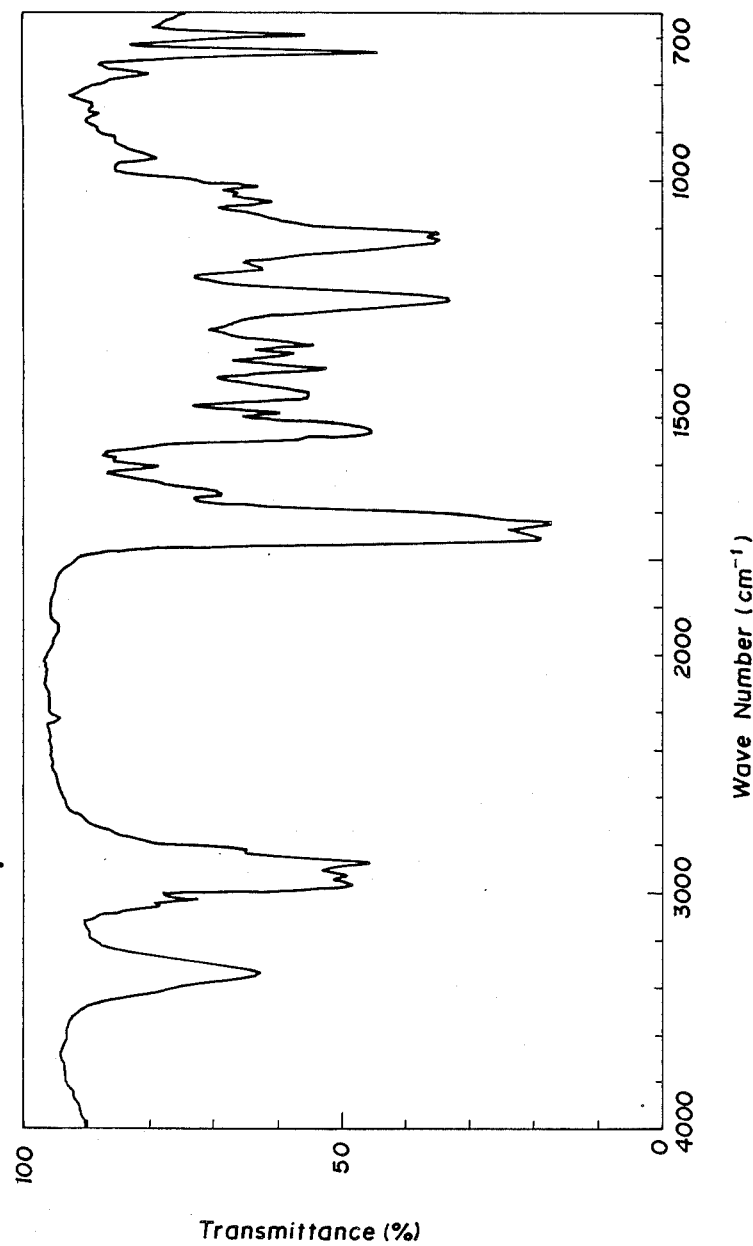

Analytical results on LAC-4 are illustrated in Table and IR absorption spectrum is shown in FIG. 4.

EXAMPLE 5

A 2l reaction vessel was charged with 194 parts ( mol) of ENA-1 obtained in Example 1 and 194 parts of ethoxyethyl acetate.

Separately 336 parts (2.0 moles) of hexamethylene diisocyanate, 258 parts (2.0 moles) of dibutylamine and 206 parts of ethoxyethyl acetate were uniformly mixed and reacted at 30° C for 2 hours under nitrogen atmosphere to obtain a reaction product having an isocyanato radical content of 10.5% by weight.

The reaction product was charged into a dropping funnel and added dropwise into the above reaction vessel. The dropwise addition was conducted with stirring at the room temperature over an hour under nitrogen atmosphere with care to prevent violent temperature rise of the reaction mixture. After completing the addition, the reaction mixture was further reacted at 60° C for 130 hours under nitrogen atmosphere.

Then IR absorption spectrum was examined on the mixture thus obtained. The characteristic absorption of NCO at 2300 cm$^{-1}$ and that of $<$N—CH=C$>$ at 1675 cm$^{-1}$ were disappeared and the ethoxyethyl acetate solution of desired product (LAC-5s) was obtained.

Crystals were separated by mixing 10 parts of LAC-5s with 100 parts of anhydrous toluene. The crystals were filtered and dried at 60° C. for 20 hours under reduced pressure to obtain about 5 parts of 1,4-bis[3,3-dimethyl-2-oxo-1-(3,3-dibutylureidohexyl)azetidine-4-yl]piperazine (LAC-5).

Figure 5:
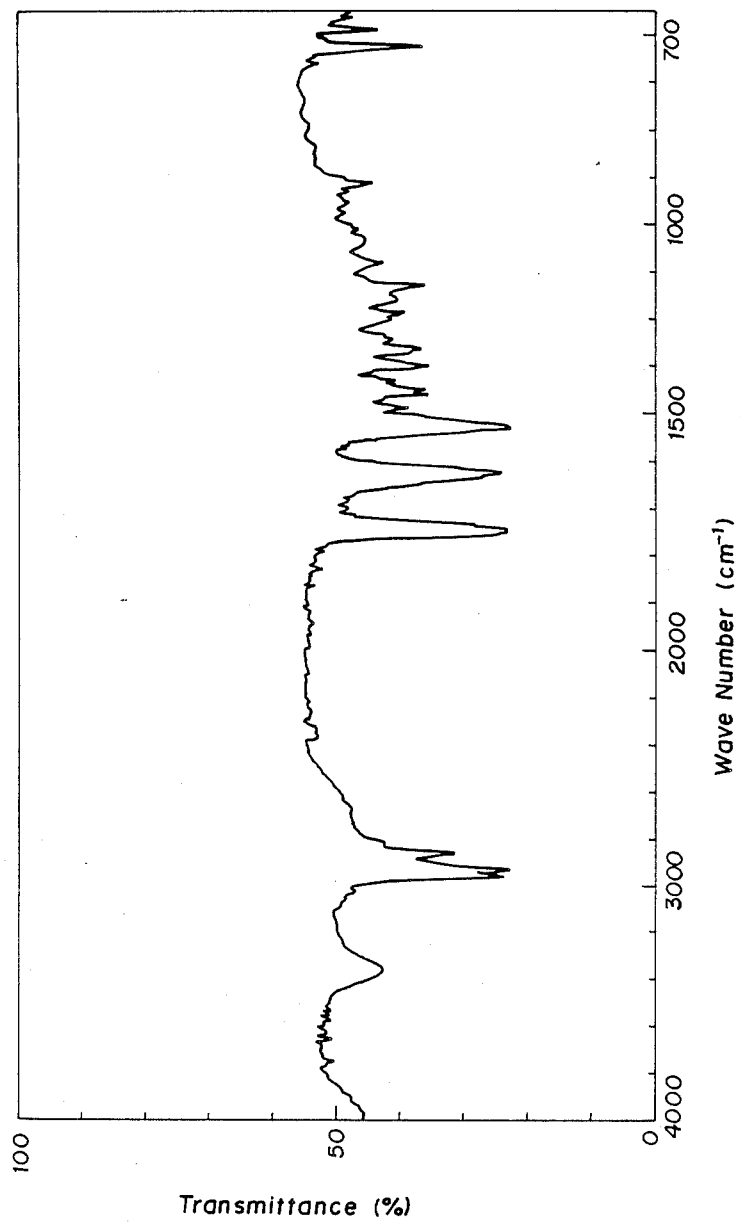

Analytical results on LAC-5 are illustrated in Table and IR absorption spectrum is shown in FIG. 5.

EXAMPLE 6

A reaction vessel fitted with a water separator was charged with 5.96 parts of 1,3-(4,4'-dipiperidyl)propan and 8.18 parts of isobutylaldehyde and heated to reflu with stirring under introduction of nitrogen stream. A half of calculated amount of water was separated during 4 hours and theoretical amount of water was separated during 18 hours.

Excess isobutylaldehyde was distilled off and the residue was distilled under vacuum to obtain a light colored and transparent liquid having a boiling point of 170° C/0.4mmHg. The liquid was 1,3-bis[1-(2-methyl-1-propenyl)piperidine-4-yl]propane and gradually solidified on standing.

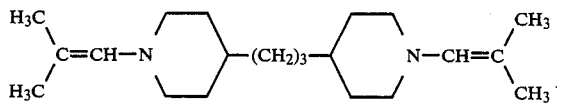

This compound was abbreviated as ENA-2. The results of elementary analysis were as follows.

| Elementary analysis (C$_{21}$H$_{38}$N$_2$) | | | |
|---|---|---|---|
| | C | H | N |
| Calculated (%) | 79.3 | 11.9 | 8.8 |
| Found (%) | 79.8 | 12.1 | 8.5 |

In the next step, a 1l reaction vessel was charged with 318 parts (1 mole) of ENA-2 and 300 parts of ethoxyethyl acetate. A dropping funnel was charged with a solution of 266 parts (2 moles) of O-tolyl isocyanate in 89 parts of ethoxyethyl acetate and fitted on the reaction vessel.

The mixture in the reaction vessel was stirred at room temperature and added dropwise with the 0-tolyl isocyanate solution over an hour under nitrogen atmosphere with care to prevent violent temperature rise of the reaction mixture. The reaction mixture was stirred for 2 hours after completing the dropwise addition and allowed to stand for 16 hours at the room temperature.

The IR absorption spectrum was examined on the mixture thus obtained. The characteristic absorption of NCO at 2300 cm$^{-1}$ and that of $<$N—CH$=$C$>$ at 1675 cm$^{-1}$ were disappeared. Thus the ethoxyethyl acetate solution of desired compound (LAC-6s) was obtained.

Crystals were separated by mixing 10 parts of LAC-6s with 100 parts of anhydrous toluene. The crystals were filtered and dried under reduced pressure at 60° C for 20 hours to obtain about 5 parts of 1,3-bis[1-(3,3-dimethyl-2-oxo-1-o-tolylazetidine-4-yl)piperidine-4-yl]propane (LAC-6).

Analytical results on LAC-6 are illustrated in Table 2.

EXAMPLE 7

A reaction vessel fitted with a water separator was charged with 25 parts of N,N'-dimethylethylenediamine and 84 parts of isobutylaldehyde and heated to reflux with stirring under introduction of nitrogen stream. A half of calculated amount of water was separated during 4 hours and theoretical amount of water was separated during 18 hours.

Excess isobutylaldehyde was distilled off and the residue was distilled under vacuum to obtain a light colored and transparent liquid having a boiling point of 59° C/0.1mmHg. The liquid was N,N'-bis(2-methyl-1-propenyl)-N,N'-dimethylethylenediamine.

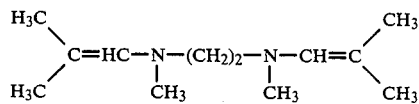

This compound was abbreviated as ENA-3. The results of elementary analysis were as follows.

| Elementary analysis (C$_{12}$H$_{24}$N$_2$) | | | |
|---|---|---|---|
| | C | H | N |
| Calculated (%) | 73.5 | 12.2 | 14.3 |
| Found (%) | 73.9 | 12.1 | 14.0 |

In the next step, a 2l reaction vessel was charged with 196 parts of ENA-3 and 196 parts of ethoxyethyl acetate.

Separately 348 parts (2.0 moles) of 2,4-TDI were uniformly mixed with 120 parts (2.0 moles) of isopropyl alcohol and 247 parts of ethoxyethyl acetate, and reacted at 80° C for 4 hours under nitrogen atmosphere to obtain a reaction product having an isocyanato radical content of 11.7% by weight. A dropping funnel was charged with the reaction product and fitted on the above reaction vessel.

The mixture in the reaction vessel was stirred at the room temperature and added dropwise with the reaction product over an hour under nitrogen atmosphere with care to prevent violent temperature rise of the reaction mixture. The reaction mixture was stirred for 2 hours after completing the dropwise addition and allowed to stand for 16 hours at the room temperature.

The IR absorption spectrum was examined on the mixture thus obtained The characteristic absorption of NCO at 2300cm$^{-1}$ and that of $<$N—CH$=$C$>$ at 1675 cm$^{-1}$ were disappeared. Thus the ethoxyethyl acetate solution of desired product (LAC-7s) was obtained.

Crystals were separated by mixing 10 parts of LAC-7s with 100 parts of anhydrous toluene.

The crystals were filtered and dried at 60° C. for 20 hours under reduced pressure to obtain about 5 parts of N,N'-bis[3,3-dimethyl-2-oxo-1-(m-isopropoxycarbonylamino-o- or p-tolyl)azetidine-4-yl]-N,N'-dimethylethylenediamine (LAC-7).

Analytical results on LAC-7 are illustrated in Table 2.

EXAMPLE 8

A reaction vessel fitted with a water separator was charged with 30 parts of 2-methylpiperazine and 75.8 parts of isobutylaldehyde and heated to reflux for 12 hours.

Excess isobutylaldehyde was distilled off and the residue was distilled to obtain 1,4-bis(2-methyl-1-propenyl)-2-methylpiperazine of the following formula having a boiling point of 62° C./0.2mmHg.

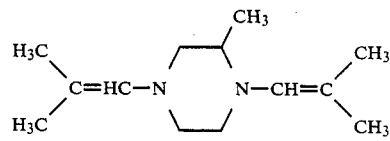

This compound was abbreviated as ENA-4. The results of elementary analysis were as follows.

| Elementary analysis ($C_{13}H_{24}N_2$) | | | |
|---|---|---|---|
| | C | H | N |
| Calculated (%) | 75.0 | 11.5 | 13.5 |
| Found (%) | 74.5 | 11.7 | 13.8 |

In the next step, a 2 l reaction vessel was charged with 208 parts (1.0 mole) of ENA-4 and 208 parts of ethoxyethyl acetate.

Separately 376 parts (2.0 moles) of XDI was uniformly mixed with 148 parts (2.0 moles) of 1-methylpropanol and 276 parts of ethoxyethyl acetate, and reacted at 80° C for 4 hours under nitrogen atmosphere to obtain a reaction product having an isocyanato radical content of 10.5% by weight. A dropping funnel was charged with the reaction product and fitted on the above reaction vessel.

The mixture in the reaction vessel was stirred at the room temperature and added dropwise with the reaction product over an hour under nitrogen atmosphere with care to prevent violent temperature rise of the reaction mixture. After completing the addition, the reaction was continued at 70° C for 100 hours under nitrogen atmosphere.

The IR absorption spectrum was examined on the mixture thus obtained. The characteristic absorption of NCO at 2300 cm$^{-1}$ and that of <N—CH=C> at 1675 cm$^{-1}$ were disappeared. Thus the ethoxyethyl acetate solution of desired product (LAC-8s) was obtained.

Crystals were separated by mixing 10 parts of LAC-8s with 100 Parts of anhydrous toluene.

The crystals were filtered and dried at 60° C for 20 hours under reduced pressure to obtain about 5 parts of 1,4-bis[3,3-dimethyl-2-oxo-1-(3-(1-methylpropoxycarbonylaminomethyl)-enzyl)azetidine-4-yl]-2-methylpiperazine (LAC-8).

Analytical results on LAC-8 are illustrated in Table 2.

EXAMPLE 9

A 2 l reaction vessel was charged with 194 parts (1.0 mole) of ENA-1 obtained in Example 1 and 194 parts of toluene.

Separately 336 parts (2 moles) of hexamethylene diisocyanate, 260 parts (2 moles) of 2-ethylhexanol and 204 parts of toluene were uniformly mixed and reacted at 100° C for 6 hours under nitrogen atmosphere to obtain a reaction product having an isocyanato radical content of 10.5% by weight. A dropping funnel was charged with the reaction product and fitted on the above reaction vessel.

The mixture in the reaction vessel was stirred at the room temperature and added dropwise with the reaction product over an hour under nitrogen atmosphere with care to prevent violent temperature rise of the reaction mixture. After completing the addition, the reaction was continued at 60° C. for 130 hours under nitrogen atmosphere.

The IR absorption spectrum was examined on the mixture thus obtained The characteristic absorption of NCO at 2300 cm$^{-1}$ and that of <N—CH=C> at 1675 cm$^{-1}$ were disappeared. Thus the toluene solution of desired product (LAC-9s) was obtained.

The solvent was removed from 10 parts of LAC-9s at 60° C. for 20 hours under reduced pressure to obtain about 7 parts of 1,4-bis[3,3-dimethyl-2-oxo-1-(2-ethylhexyloxycarbonylaminohexyl)azetidine-4-yl]piperazine (LAC-9).

Analytical results on LAC-9 are illustrated in Table 2.

EXAMPLE 10

A reaction vessel fitted with a water separator was charged with 25 parts of piperazine and 85.5 parts of 2-methylbutylaldehyde and heated to reflux with stirring under introduction of nitrogen. A half of calculated amount of water was separated during 5 hours and theoretical amount of water was separated during 20 hours.

Excess 2-methylbutylaldehyde was distilled off and the residue was distilled under vacuum to obtain a transparent liquid having a boiling point of 65° C./0.1mmHg. The liquid was 1,4-bis(2-methyl-1-butenyl)piperazine and solidified on standing.

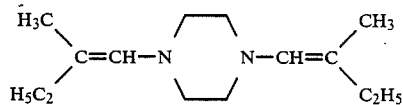

This compound was abbreviated as ENA-5. The results of elementary analysis was as follows.

| Elementary analysis ($C_{14}H_{26}N_2$) | | | |
|---|---|---|---|
| | C | H | N |
| Calculated (%) | 75.7 | 11.7 | 12.6 |
| Found (%) | 76.0 | 11.5 | 12.5 |

In the next step, a 2 l reaction vessel was charged with 222 parts (1.0 mole) of ENA-5 and 222 parts of ethoxyethyl acetate.

Separately 348 parts (2 moles) of 2,4-TDI, 120 parts (2 moles) of isopropyl alcohol and 247 parts of ethoxyethyl acetate were uniformly mixed and reacted at 80° C for 4 hours under nitrogen atmosphere to obtain a reaction product having an isocyanato radical content of 11.7% by weight. A dropping funnel was charged with the reaction product and fitted on the above reaction vessel.

The mixture in the reaction vessel was stirred at the room temperature and added dropwise with the reaction product over an hour under nitrogen atmosphere with care to prevent violent temperature rise of the reaction mixture. After completing the addition, the reaction mixture was further stirred for 2 hours and allowed to stand for 16 hours at the room temperature.

The IR absorption spectrum was examined on the mixture thus obtained. The characteristic absorption of NCO at 2300 cm$^{-1}$ and that of <N—CH=C> at 1675cm$^{-1}$ were disappeared. Thus the ethoxyethyl acetate solution of the desired product (LAC-10s) was obtained.

Crystals were separated by mixing 10 parts of LAC-10s with 100 parts of anhydrous toluene. The separated crystals were filtered and dried at 50° C. for 20 hours under reduced pressure to obtain about 5 parts of 1,4-bis[3-methyl-3-ethyl-2-oxo-1-(m-isopropoxycarbonylamino-o- or p-tolyl)azetidine-4-yl]piperazine (LAC-10).

Analytical results on LAC-10 is illustrated in Table 2.

EXAMPLE 11

A reaction vessel fitted with a water separator was charged with 25 parts of piperazine and 87 parts of 2-ethylbutylaldehyde and heated to reflux with stirring under introduction of nitrogen stream. A half of calculated amount of water was separated during 5 hours and theoretical amount of water was separated during 20 hours.

Excess 2-ethylbutylaldehyde was distilled off and the residue was distilled under vacuum to obtain a transparent liquid having a boiling point of 68° C./0.1 mmHg. The liquid was 1,4-bis(2-ethyl-1-butenyl)piperazine and solidified on standing.

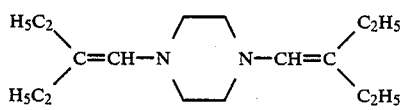

This compound was abbreviated as ENA-6. Results of elementary analysis on ENA-6 were as follows.

| Elementary analysis (C₁₆H₃₀N₂) | | | |
| --- | --- | --- | --- |
|  | C | H | N |
| Calculated (%) | 76.8 | 12.0 | 11.2 |
| Found (%) | 77.1 | 11.9 | 11.0 |

In the next step, a 2 l reaction vessel was charged with 250 parts (1.0 mole) of ENA-6 and 250 parts of ethoxyethyl acetate. A dropping funnel was charged with 238 parts (2 moles) of phenyl isocyanate and fitted on the above reaction vessel.

The mixture in the reaction vessel was stirred at the room temperature and added dropwise with phenyl isocyanate over an hour under nitrogen atmosphere with care to prevent violent temperature rise of the reaction mixture. After completing the addition, the reaction mixture was further stirred for 2 hours and allowed to stand for 16 hours at the room temperature.

The IR absorption spectrum was examined on the mixture thus obtained. The characteristic absorption of NCO at 2300 cm⁻¹ and that of <N—CH=C> at 1675 cm⁻¹ were disappeared. Thus the ethoxyethyl acetate solution of desired product (LAC-11s) was obtained.

Crystals were separated by mixing 10 parts of LAC-11s with 100 parts of anhydrous toluene. The separated crystals were filtered and dried at 50° C. for 20 hours under reduced pressure to obtain about 5 parts of 1,4-bis(3,3-diethyl-2-oxo-1-phenylazetidine-4-yl)piperazine (LAC-11).

Analytical results on LAC-11 are illustrated in Table 2.

EXAMPLE 12

A reaction vessel fitted with a water separator was charged with 13.4 parts of 1,3-(4,4'-dipiperidyl)propane and 34.2 parts of 2-phenylpropylaldehyde and heated to reflux with stirring under introduction of nitrogen stream. Theoretical amount of water was separated during 30 hours.

Excess 2-phenylpropylaldehyde was distilled off to obtain 1,3-bis[1-(2-phenyl-1-propenyl)piperidine-4-yl]propane having a melting point of 120° C.

This compound had the following formula and was abbreviated as ENA-7.

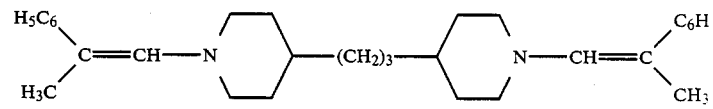

Results of elementary analysis on ENA-7 was as follows.

| Elementary analysis (C₃₁H₄₂N₂) | | | |
| --- | --- | --- | --- |
|  | C | H | N |
| Calculated (%) | 84.2 | 9.5 | 6.3 |
| Found (%) | 84.1 | 9.6 | 6.3 |

In the next step, a 2 l reaction vessel was charged with 382 parts (0.87 mole) of ENA-7 and 382 parts of ethoxyethyl acetate. A dropping funnel was charged with 206 parts (1.73 moles) of phenyl isocyanate and fitted on the above reaction vessel.

The mixture in the reaction vessel was stirred at the room temperature and added dropwise with phenyl isocyanate over an hour under nitrogen atmosphere with care to prevent violent temperature rise of the reaction mixture. After completing the addition, the reaction mixture was further stirred for 2 hours and allowed to stand for 16 hours at the room temperature.

The IR absorption spectrum was examined on the mixture thus obtained. The characteristic absorption of NCO at 2300 cm⁻¹ and that of <N—CH=C> at 1675 cm⁻¹ were disappeared. Thus the ethoxyethyl acetate solution of desired product (LAC-12s) was obtained.

Crystals were separated by mixing 10 parts of LAC-12s with 100 parts of anhydrous hexane. The separated crystals were filtered and dried at 60° C. for 20 hours under reduced pressure to obtain about 5 parts of 1,3-bis[1-(3-methyl-3-phenyl-2-oxo-1-phenylazetidine-4-yl)piperidine-4-yl]propane (LAC-12).

Analytical results on LAC-12 are illustrated in Table 2.

TABLE 2

| | IR-characteristic absorption (cm⁻¹) —C—C— \| \| N—C=O | Amine value (mgKOH/g) | | Elementary analysis (%) | | State | β-Amino-β-propiolactam derivative No. (Table 1) |
| --- | --- | --- | --- | --- | --- | --- | --- |
| | | Calculated | Found | Calculated C:H:N | Found C:H:N | | |
| Example-1 | 1745 | 259.7 | 256.6 | 72.7:7.4:13.0 | 72.2:7.7:13.2 | Solid | LAC-1 |
| Example-2 | " | 169.5 | 167.9 | 65.3:7.6:12.7 | 65.2:7.8:12.5 | " | —2 |
| Example-3 | 1750 | 156.3 | 154.8 | 66.9:8.1:11.7 | 67.0:8.3:11.5 | " | —3 |

TABLE 2-continued

| | IR-characteristic absorption (cm$^{-1}$) $\begin{array}{c}-\text{C}-\text{C}-\\ \mid\ \ \mid\\ \text{N}-\text{C}=\text{O}\\ \mid\end{array}$ | Amine value (mgKOH/g) Calculated | Amine value (mgKOH/g) Found | Elementary analysis (%) Calculated C:H:N | Elementary analysis (%) Found C:H:N | State | β-Amino-β-propiolactam derivative No. (Table 1) |
|---|---|---|---|---|---|---|---|
| Example-4 | " | 133.9 | 132.8 | 63.0:7.9:10.0 | 63.2:8,1:9.7 | Liquid | −4 |
| Example-5 | 1745 | 142.4 | 141.1 | 67.0:10.7:14.2 | 67.1:10.8:14.0 | Solid | −5 |
| Example-6 | " | 192.1 | 189.5 | 76.0:8.9:9.6 | 76.1:9.1:9.5 | " | −6 |
| Example-7 | " | 169.0 | 165.8 | 65.1:7.8:12.7 | 65.3:8.0:12.4 | " | −7 |
| Example-8 | 1750 | 153.3 | 151.5 | 67.2:8.2:11.5 | 67.3:8.5:11.2 | " | −8 |
| Example-9 | 1745 | 142.0 | 140.6 | 66.8:10.4:10.6 | 67.0:10.7:10.4 | Liquid | −9 |
| Example-10 | " | 162.6 | 161.8 | 66.1:7.8:12.2 | 66.3:8.1:12.0 | Solid | −10 |
| Example-11 | " | 229.9 | 229.0 | 73.8:8.2:11.5 | 73.9:8.4:11.3 | " | −11 |
| Example-12 | " | 165.0 | 163.2 | 79.4:7.7:8.2 | 79.2:7.9:8.3 | " | −12 |

EXAMPLE 13

A mixture was prepared from 320 parts of LAC-12 and 380 parts of a TDI/trimethylolpropane adduct (Trademark: OLESTER P45-75S; a product of Mitsui Toatsu Chemicals Inc.; NCO content: 11.6% by weight).

The mixture was packed in a sealed container and stored at the room temperature. No change was abserved after 6 months on its physical properties.

The mixture after storage was applied on a glass plate and allowed to stand at the room temperature in a relative humidity of 50%. The coated surface became tack free after an hour.

OLESTER P45-75S alone was applied on a glass plate and the same procedure as above was carried out. Surface tackiness was observed even after 5 hours

EXAMPLE 14

Following raw materials were used in the examples β-Amino-β-propiolactam derivative . . . LAC-2 and LAC-6 in Table 2. Prepolymer . . . Prepolymer was prepared by reacting 598 parts of 2,4-TDI at 100° C. for 10 hours with 2600 parts of polyoxypropylene diol having a molecular weight of 2000 and 1802 parts of polyoxypropylene triol having a molecular weight of 3000. The prepolymer had a terminal isocyanato radical content of 1.9% by weight and a viscosity of 41,000 cps/25° C. Thixotropic agent . . . Colloidal silica (Trademark: AEROSIL #R-972, a product of Japan Aerosil Co.).

Properties were determined by the following methods. Curing ability . . . Tack free time was measured in accordance with items 6–10 in JIS-A5758 (1986). Storage stability . . . The stability was measured by the penetration test in accordance with JIS-K2808 (1961). Two second values and five second values (10$^{-1}$mm unit) of penetration were measured after storing one component type polyurethane sealing materials for a given period in a completely sealed condition. Mechanical properties of sealing materials. . . . Properties of cured materials after application were measured in accordance with JIS-K6301. The samples were stored after application for 7 days at 23° C. in the relative humidity of 50% and further stored for 7 days at 50° C. Properties tested were 100% and 200% modulus, tensile strength and elongation.

A 3 l planetary mixer was charged with 380 parts of dioctyl phthalate, 475 parts of calcium carbonate, 99 parts of titanium oxide and 8 parts of weather stabilizer (Trademark: IRGANOX 1010, a product of Ciba Geigy Co.). These raw materials were mixed for 15 minutes at the room temperature and then dehydrated at 100° C for an hour with mixing under reduced pressure. In the next step, the planetary mixer was added with 445 parts of prepolymer and 142 parts of 60% by weight of dimethylacetamide solution of β-amino-β-propiolactam derivative LAC-2,that is 1,4-bis[3,3-dimethyl-2-oxo-1-(m-isopropoxycarbonylamino-o- or p-tolyl)azetidine-4-yl]piperazine and mixed for 15 minutes at the room temperature. The resulting mixture was further added with 130 parts of thixotropic agent (AEROSIL #R-972) and 175 parts of xylene, and kneaded for 10 minutes at the room temperature under reduced pressure to obtain the one component type polyurethane sealing material of this invention.

As illustrated in Table 3, the tack free time of this sealing material was shorter than that of commercially available sealing materials and marked improvement was found on its curing ability. In addition, as illustrated in Table 4, good workability was proved by the penetration test storage at 50? C for 14 days under sealed condition. The cured material after application had no foaming at all and was excellent in mechanical properties.

TABLE 3

| Formulation (part) | Example 14 | Example 15 | Comparative example 1 |
|---|---|---|---|
| Calcium carbonate | 475 | ← | ← |
| Titanium oxide | 99 | ← | ← |
| DOP | 380 | ← | ← |
| Prepolymer | 445 | ← | ← |
| AEROSIL #R-972 | 130 | ← | ← |
| Xylene | 175 | ← | ← |
| IRGANOX 1010 | 8 | ← | ← |
| LAC-2 | 142 | — | — |
| LAC-6 | — | 98 | — |
| Tack free time (min) | 23 | 31 | 300< |

DOP: Dioctyl phthalate

TABLE 4

| Properties | | Example 14 | Example 15 | Comparative example 1 |
|---|---|---|---|---|
| Storage stability | | | | |
| Penetration (10$^{-1}$ mm) | | | | |
| Directly after preparation | 2 sec | 420< | 420< | 420< |
| | 5 sec | 420< | 420< | 420< |

TABLE 4-continued

| Properties | | Example 14 | Example 15 | Comparative example 1 |
|---|---|---|---|---|
| After 14 days at 50° C. | 2 sec | 280 | 280 | 290 |
| | 5 sec | 370 | 360 | 370 |
| Property after curing | | | | |
| Modulus (kg/cm$^2$) | | | | |
| 100% deflection | | 2.2 | 2.4 | 1.5 |
| 200% deflection | | 4.0 | 4.4 | 3.5 |
| Tensile strength (kg/cm$^2$) | | 13 | 12 | 10 |
| Elongation (%) | | 750 | 800 | 850 |
| Foaming | | No | No | Found |

EXAMPLE 15

The same procedures as described in Example 14 were carried out except 98 parts of 60% by weight of dimethylacetamide solution of β-amino-β-propiolactam derivative LAC-6 were used in place of that of LAC-2. That is, 1,3-bis[1-(3,3-dimethyl-2-oxo-1-o-tolylazetidine-4-yl)piperidine-4-yl]propane was used.

As a result, very quick curing was exhibited as shown in Table 3. Besides, as illustrated in Table 4, good workability was proved by the penetration test after storage at 50° C for 14 days under sealed condition. The cured material after application had no foaming at all and was excellent in mechanical properties.

COMPARATIVE EXAMPLE 1

The same procedures as described in Example 14 were carried out except β-aminoβ-propiolactam derivative was omitted. Consequently, curing rate became very slow as illustrated in Table 3. Besides, as shown in Table 4, foaming was found in the cured material after application and thus modulus and tensile strength were lowered.

EXAMPLE 16

Following raw materials were used in the examples. β-Amino-β-propiolactam derivative . . . LAC-6, LAC-7, LAC-8 and LAC-9 in Table 2. Prepolymer . . . Prepolymer was prepared by reacting 416 parts of 2,4-TDI at 100° C. for 10 hours with 1700 parts of polyoxypropylenediol having a molecular weight of 3000 and 2800 parts of polyoxypropylenetriol having a molecular weight of 5000. The prepolymer had terminal isocyanato radical content of 1.7% by weight and a viscosity of 56,000 cps/25° C. Thixotropic agent . . . Colloidal silica (Trademark: AEROSIL #R-972, a product of Japan Aerosil Co.) and fatty acid amide wax (Trademark: DISPARON #6500, a product of Kusumoto Kasei Co.). Curing ability, storage stability and mechanical properties were determined by the same methods as described in Example 14.

A 3l planetary mixer was charged with 220 parts of dioctyl phthalate, 610 parts of calcium carbonate, 60 parts of titanium oxide and 12 parts of weather stabilizer (IRGANOX 1010) These materials were mixed for 15 minutes at the room temperature and then dehydrated at 100° C. for an hour with mixing under reduced pressure In the next step, the planetary mixer was added with 649 parts of prepolymer and 109 parts of 70% by weight of dimethylacetamide solution of β-amino-β-propiolactam derivative LAC-6, that is, 1,3-bis[1-(3,3-dimethyl-2-oxo-1-o-tolylazetidine-4-yl)piperidine-4-yl]propane and mixed for 15 minutes at the room temperature. The resulting mixture was further added with 140 parts of thixotropic agent (AEROSIL #R-972) and 200 parts of toluene, and kneaded for 10 minutes at the room temperature under reduced pressure to obtain the one component type polyurethane wall covering material of this invention.

As illustrated in Table 5, the tack free time of this wall covering material was shorter than that of commercially available wall covering materials and marked improvement was found on its curing ability.

In addition, good workability was proved by the penetration test after storage at 50° C. for 14 days under sealed condition. The cured material after application had no foaming at all and was excellent in mechanical properties.

EXAMPLE 17

The same procedures as described in Example 16 was carried out except 123 parts of 70% by weight of dimethylacetamide solution of β-amino-β-propiolactam derivative LAC-7 were used in place of that of LAC-6. That is, N,N'-bis[3,3-dimethyl-2-oxo-1-(m-isopropoxycarbonylamino-o- or p-tolyl)azetidine-4-yl]-N,N'-dimethylethylenediamine was used.

Results are illustrated in Table 5. Very quick curing was exhibited. Besides good workability was proved by the penetration test after storage at 50° C. for 14 days under sealed condition. The cured material after application had no foaming at all and was excellent in mechanical properties.

EXAMPLE 18

The same procedures as described in Example 16 was carried out except 135 parts of 70% by weight of dimethylacetamide solution of β-amino-β-propiolactam derivative LAC-8 were used in place of LAC-6 and 120 parts of DISPARON #6500 were used in place of AEROSIL #R-972. Consequently very quick curing was exhibited as illustrated in Table 5. Besides good workability was proved by the penetration test after storage at 50° C. for 14 days under sealed condition. The cured material after application had no foaming at all and was excellent in mechanical properties.

EXAMPLE 19

The same procedures as described in Example 18 were carried out except 137 parts of 70% by weight of dimethylacetamide solution of β-amino-β-propiolactam derivative LAC-9 were used in place of that of LAC-8. Very quick curing was exhibited as illustrated in Table 5. Besides good workability was proved by the penetration test after storage at 50° C. for 14 days under sealed condition. The cured material after application had no foaming at all and was excellent in mechanical properties.

TABLE 5

| | Example | | | | Comparative example |
|---|---|---|---|---|---|
| | 16 | 17 | 18 | 19 | 2 |
| Formulation (part) | | | | | |
| Calcium carbonate | 610 | ← | ← | ← | ← |
| Titanium oxide | 60 | ← | ← | ← | ← |
| DOP | 220 | ← | ← | ← | ← |

TABLE 5-continued

|  |  | Example | | | | Comparative example |
|---|---|---|---|---|---|---|
|  |  | 16 | 17 | 18 | 19 | 2 |
| Prepolymer |  | 649 | ← | ← | ← | ← |
| AEROSIL #R-972 |  | 140 | ← | — | — | 140 |
| DISDARON #6500 |  | — | — | 120 | ← | — |
| Toluene |  | 200 | ← | ← | ← | ← |
| IRGANOX 1010 |  | 12 | ← | ← | ← | ← |
| LAC-6 |  | 109 | — | — | — | — |
| LAC-7 |  | — | 123 | — | — | — |
| LAC-8 |  | — | — | 135 | — | — |
| LAC-9 |  | — | — | — | 137 | — |
| DBTDL* |  | — | — | — | — | 10 |
| Tack free time (min) |  | 10 | 15 | 25 | 41 | 280 |
| Storage stability |  |  |  |  |  |  |
| Penetration ($10^{-1}$mm) |  |  |  |  |  |  |
| Directly after preparation | 2 sec | 420< | 420< | 420< | 420< | 420< |
|  | 5 sec | 420< | 420< | 420< | 420< | 420< |
| After 50° C. × 14 days | 2 sec | 310 | 310 | 330 | 320 | 170 |
|  | 5 sec | 390 | 380 | 410 | 400 | 260 |
| Property after curing |  |  |  |  |  |  |
| Modulus (kg/cm$^2$) |  |  |  |  |  |  |
| 100% deflection |  | 7.9 | 7.6 | 6.8 | 7.2 | 3.1 |
| 200% deflection |  | 12.4 | 12.0 | 11.5 | 11.9 | 5.8 |
| Tensile strength (kg/cm$^2$) |  | 39.6 | 39.0 | 38.1 | 38.2 | 22.6 |
| Elongation (%) |  | 870 | 890 | 920 | 900 | 890 |
| Foaming |  | No | ← | ← | ← | Found |

Note: *Dibutyl tin dilaurate (catalyst)

COMPARATIVE EXAMPLE 2

The same procedures as described in Example 16 were carried out except a moisture curing catalyst dibutyl tin dilaurate (DBTDL) was used in place of β-aminoβ-propiolectam derivative LAC-6.

Results are illustrated in Table 5. Curing rate was very slow as compared with the examples. A violent foaming was found in the cured product after application. Thus modulus and tensile strength were markedly reduced. Storage stability was also much lowered.

EXAMPLE 20

Following raw materials were used in the examples. β-amino-β-propiolactam derivative ... LAC-6, LAC-7, LAC-8 and LAC-9 in Table 2. Prepolymer.....The same prepolymer as described in Example 16 was used.

Precipitation inhibitor ... Colloidal silica AEROSIL #R-972. Curing ability and mechanical properties were determined by the same method as described in Example 14. Storage stability of one component type polyurethane water proof material was evaluated by measuring the viscosity after sealed storage for a given period with a BM type rotational viscometer.

A 3l planetary mixer was charged with 320 parts of dioctyl phthalate, 660 parts of calcium carbonate, 60 parts of titanium oxide, 12 parts of weather stabilizer (IRGANOX 1010). These materials were mixed for 15 minutes at the room temperature and then dehydrated at 100° C. for an hour with mixing under reduced pressure In the next step, the planetary mixer was added with 716 parts of prepolymer and 120 parts of 70% by weight of dimethylacetamide solution of β-amino-β-propiolactam derivative LAC-6, that is, 1,3-bis[1-(3,3-dimethyl-2-oxo-1-0-tolylazetidine-4-yl)piperidine-4-yl]propane and mixed for 15 minutes at the room temperature. The resulting mixture was further added with 20 parts of precipitation inhibitor (AEROSIL #R-972) and 80 parts of toluene, and kneaded for 10 minutes at the room temperature under reduced pressure, to obtain the one component type polyurethane water proof material of this invention.

As illustrated in Table 6, the tack free time of this water proof material was shorter than that of commercially available water proof materials, and marked improvement was found on its curing ability.

In addition, good workability was proved by the viscosity test after storage at 50° C. for 14 days under sealed condition. The cured material after application had no foaming at all and was excellent in mechanical properties.

EXAMPLE 21

The same procedures as described in Example 20 were carried out except 136 parts of 70% by weight of dimethylacetamide solution of β-amino-β-propiolactam derivative LAC-7 was used in place of that of LAC-6.That is, N,N'-bis[3,3-dimethyl-2-oxo-1-(m-isopropoxycarbonylamino-o- or p-tolyl)azetidine-4-yl]-N,N'-dimethylethylenediamine was used.

Results are illustrated in Table 6. Very quick curing was exhibited. Besides good workability was proved by the viscosity test after storage at 50° C. for 14 days under sealed condition. The cured material after application had no foaming at all and was excellent in mechanical properties.

TABLE 6

|  | Example | | | | Comparative example | |
|---|---|---|---|---|---|---|
|  | 20 | 21 | 22 | 23 | 3 | 4 |
| Formulation (part) |  |  |  |  |  |  |
| Calcium carbonate | 660 | ← | ← | ← | ← | ← |
| Titanium oxide | 60 | ← | ← | ← | ← | ← |
| DOP | 320 | ← | ← | ← | ← | ← |
| Prepolymer | 716 | ← | ← | ← | ← | ← |
| AEROSIL #R-972 | 20 | ← | ← | ← | ← | ← |
| Toluene | 80 | ← | ← | ← | ← | ← |
| IRGANOX 1010 | 12 | ← | ← | ← | ← | ← |
| LAC-6 | 120 | — | — | — | — | — |
| LAC-7 | — | 136 | — | — | — | — |
| LAC-8 | — | — | 149 | — | — | — |
| LAC-9 | — | — | — | 151 | — | — |
| ENA-1 | — | — | — | — | — | 26 |
| Tack free time (min) | 12 | 17 | 30 | 47 | >300 | 62 |
| Storage stability |  |  |  |  |  |  |
| Viscosity after 14 days (ps/25° C.) |  |  |  |  |  |  |
| 23° C. storage | 380 | 390 | 410 | 380 | 350 | Gel |
| 50° C. storage | 490 | 500 | 530 | 480 | 450 | Gel |
| Property after curing |  |  |  |  |  |  |
| Modulus (kg/cm$^2$) |  |  |  |  |  |  |
| 100% deflection | 3.1 | 3.0 | 2.9 | 2.9 | 2.2 | 2.3 |
| 200% deflection | 4.8 | 4.6 | 4.5 | 4.4 | 3.5 | 3.7 |
| Tensile strength (kg/cm$^2$) | 37.3 | 36.5 | 35.9 | 35.2 | 29.8 | 30.5 |
| Elongation (%) | 1060 | 1090 | 1110 | 1020 | 1160 | 1180 |
| Foaming | No | ← | ← | ← | Found | No |

EXAMPLE 22

The same procedures as described in Example 20 were carried out except 149 parts of 70% by weight of dimethylacetamide solution of β-amino-β-propiolactam derivative LAC-8 were used in place of that of LAC-6. Results are illustrated in Table 6. Very quick curing was exhibited. Besides good workability was proved by the viscosity test after storage at 50° C. for 14 days under sealed condition. The cured material after application had no foaming at all and was excellent in mechanical properties.

EXAMPLE 23

The same procedures as described in Example 20 were carried out except 151 parts of 70% by weight of dimethylacetamide solution of β-amino-β-propiolactam derivative LAC-9 were used in place of LAC-6. Results are illustrated in Table 6. Very quick curing was exhibited. Besides good workability was proved by the viscosity test after storage at 50° C. for 14 days under sealed condition. The cured material after application had no foaming at all and was excellent in mechanical properties.

COMPARATIVE EXAMPLE 3

The same procedures as described in Example 20 were carried out except β-amino-β-propiolactam derivative was omitted.

The results are illustrated in Table 6. Curing rate was markedly lowered. Foaming was found in the cured material after application. Thus, modulus and tensile strength were remarkably reduced.

COMPARATIVE EXAMPLE 4

The same procedures as described in Example 20 were carried out except 26 parts of ENA-1 in Example 1 were used in place of β-amino-β-propiolactam derivative LAC-6.

The results are illustrated in Table 6. Curing rate were lowered. Storage stability was drastically damaged and the material caused gelation during storage for 14 days at the room temperature. Furthermore, modulus and tensile strength were reduced.

FEASIBILITY FOR INDUSTRIAL UTILIZATION

The β-amino-β-propiolactam derivative of this invention forms two secondary amino radicals by the hydrolysis due to atmospheric moisture. This invention utilizes above characteristic and provided moisture curable compositions, sealing materials, wall covering materials and water proof materials of one package polyurethane. These products have good storage stability for a long period, can be rapidly cured on application by the atmospheric moisture and are excellent in physical properties after curing. Therefore the present invention can provide industrially useful materials for the simplification and acceleration of construction works, vehicle assembling steps etc.

What is claimed is :

1. A β-amino-β-propiolactam derivative having the formula (I) :

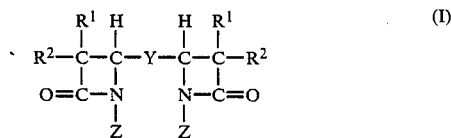

wherein $R^1$ is a monovalent radical selected from the group consisting of a hydrogen atom, alkyl radical having 1-8 carbon atoms and cycloalkyl radical; $R^2$ is a monovalent radical selected from the group consisting of an alkyl radical having 1-12 carbon atoms and cycloalkyl radical; Y is a divalent radical obtained by eliminating a hydrogen atom respectively from each secondary amino group in an aliphatic or alicyclic di-secondary-amine having 1-22 carbon atoms; and Z is a monovalent radical obtained by eliminating an isocyanato radical from an aliphatic or aromatic monoisocyanate.

2. The β-amino-β-propiolactam derivative as claimed in claim 1 wherein $R^1$ and $R^2$ are respectively methyl radical or ethyl radical.

3. The β-amino-β-propiolactam derivative as claimed in claim 2 wherein Y is a divalent radical obtained by eliminating a hydrogen atom respectively from each secondary amino group of a diamine selected from the group consisting of a diamine having the general formula (II), (III) or (VI) :

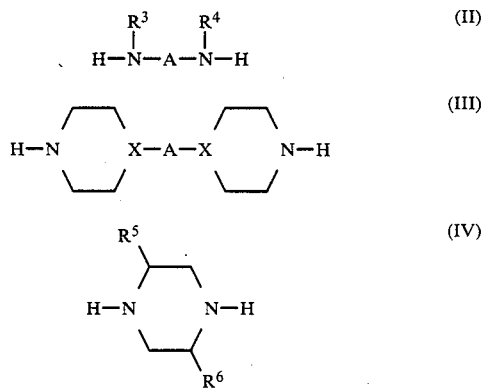

wherein $R^3$ and $R^4$ are respectively a monovalent radical selected from the group consisting of an alkyl radical having 1-8 carbon atoms, cycloalkyl radical and aryl radical; $R^5$ and $R^6$ are respectively a monovalent radical selected from the group consisting of a hydrogen atom, alkyl radical having 1 -6 carbon atoms and a cycloalkyl radical; X is a CH radical or a nitrogen atom; A is a divalent radical selected from the group consisting of an alkylene radical having 1-10 carbon atoms, cycloalkylene radical and arylene radical; and A includes a bond when X is a CH radical.

4. The amino-β-propiolactam derivative as claimed in claim 2 wherein Y is a 1,4-piperazindiyl radical.

5. The β-amino-β-propiolactam derivative as claimed in claim 4 wherein Z is a monovalent radical obtained by eliminating an isocyanato radical from a monoisocyanate having the formula (V) or (VI) :

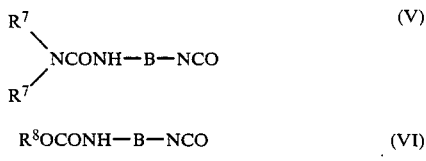

wherein $R^7$ is an alkyl radical having 1-10 carbon atoms; $R^8$ is an alkyl radical having 1-10 carbon atoms or alkoxy(polyethyleneoxy)alkyl radical; and B is a divalent radical obtained by eliminating two isocyanato radicals from an aliphatic or aromatic diisocyanate.

6. The β-amino-β-propiolactam derivative as claimed in one of claim 1 to claim 4 wherein Z is a monovalent radical obtained by eliminating an isocyanato radical from a monoisocyanate having the formula (V) or (VI):

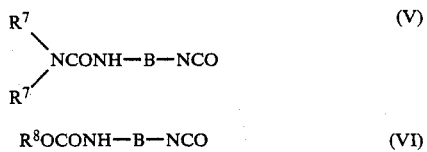

wherein $R^7$ is butyl radical; $R^8$ is a monovalent radical selected from the group consisting of isopropyl radical, 2-butyl radical, 2-ethylhexyl radical and 2-(2-ethoxyethoxy)ethyl radical; and B is a divalent radical obtained by eliminating two isocyanato radicals from hexamethylene diisocyanate or xylylene diisocyanate.

7. A moisture curable polyurethane composition comprising the $\beta$-amino-$\beta$-propiolactam derivative as claimed in one of claim 1 to claim 6 and a polyisocyanate and/or a polyurethane prepolymer having a terminal isocyanato radical.

8. The moisture curable polyurethane composition as claimed in claim 7 wherein the polyisocyanate is an adduct of tolylene diisocyanate or hexamethylene diisocyanate with trimethylolpropane.

9. The moisture curable polyurethane composition as claimed in claim 7 or claim 8 wherein the polyurethane prepolymer is a compound having the terminal isocyanato radical and being derived from polyoxyalkylenepolyol and tolylene diisocyanate.

10. A sealing or wall covering material of moisture curable polyurethane comprising the $\beta$-amino-$\beta$-propiolactam derivative as claimed in claim 6, the polyisocyanate and/or the polyurethane prepolymer having the terminal isocyanato radical, and a thixotropic agent.

11. The sealing or wall covering material of moisture curable polyurethane as claimed in claim 10 wherein the polyisocyanate is the adduct of tolylene diisocyanate or hexamethylene diisocyanate with trimethylolpropane.

12. The sealing or wall covering material of moisture curable polyurethane as claimed in claim 11 wherein the polyurethane prepolymer is a compound having the terminal isocyanato radical and being derived from the polyoxyalkylenepolyol and tolylene diisocyanate.

13. The sealing or wall covering material of moisture curable polyurethane as claimed in claim 12 wherein the thixotropic agent is a colloidal silica and/or a fatty acid amide wax.

14. A moisture curable polyurethane water proof material comprising the $\beta$-amino-$\beta$-propiolactam derivative as claimed in claim 6, the polyisocyanate and/or the polyurethane prepolymer having the terminal isocyanato radical, and a filler.

15. The moisture curable polyurethane water proof material as claimed in claim 14 wherein the polyisocyanate is the adduct of tolylene diisocyanate or hexamethylene diisocyanate with trimethylolpropane.

16. The moisture curable polyurethane water proof material as claimed in claim 15 wherein the polyurethane prepolymer is the compound having the terminal isocyanato radical and being derived from the polyoxyalkylenepolyol and tolylene diisocyanate.

17. The moisture curable polyurethane water proof material as claimed in claim 16 wherein the filler is one or a plurality of the compound selected from the group consisting of calcium carbonate, titanium oxide, calcium hydroxide, calcium oxide, talc, clay, aluminum sulfate and polyvinylchloride fine powder.

18. The $\beta$-amino-$\beta$-propiolactam derivative as claimed in claim I wherein Y is a divalent radical obtained by eliminating a hydrogen atom respectively from each secondary amino group of a diamine selected from the group consisting of a diamine having the general formula (II), (III) or (VI):

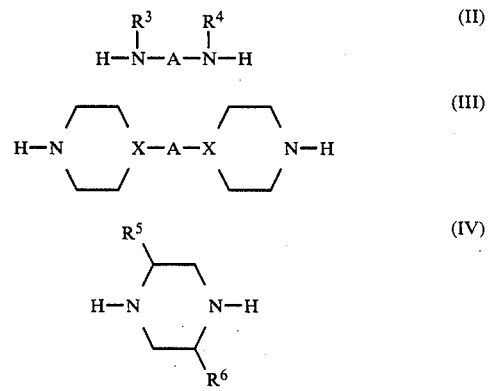

wherein $R^3$ and $R^4$ are respectively a monovalent radical selected from the group consisting of an alkyl radical having 1-8 carbon atoms, cycloalkyl radical and aryl radical; $R^5$ and $R^6$ are respectively a monovalent radical selected from the group consisting of a hydrogen atom, alkyl radical having 1-6 carbon atoms and a cycloalkyl radical; X is a CH radical or a nitrogen atom; A is a divalent radical selected from the group consisting of an alkylene radical having 1-10 carbon atoms, cycloalkylene radical and arylene radical; and A includes a bond when X is a CH radical.

19. The $\beta$-amino-$\beta$-propiolactam derivative as claimed in claim 1 wherein Y is a 1,4-piperazindiyl radical.

20. The $\beta$-amino-$\beta$-propiolactam derivative as claimed in claim 1 wherein Z is a monovalent radical obtained by eliminating an isocyanato radical from a monoisocyanate having the formula (v) or (VI):

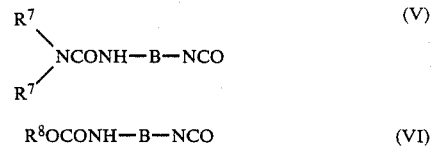

wherein $R^7$ is an alkyl radical having 1-10 carbon atoms; $R^8$ is an alkyl radical having 1-10 carbon atoms or alkoxy(polyethylene-oxy)alkyl radical; and B is a divalent radical obtained by eliminating two isocyanato radicals from an aliphatic or aromatic diisocyanate.

21. The $\beta$-amino-$\beta$-propiolactam derivatives as claimed in claim 1 wherein Z is a monovalent radical obtained by eliminating an isocyanato radical from a monoisocyanate having the formula (v) or (VI):

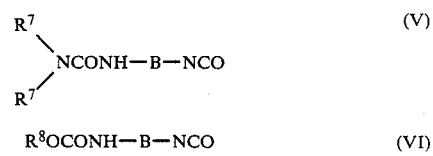

wherein $R^7$ is a butyl radical; $R^8$ is a monovalent radical selected from the group consisting of isopropyl radical, 2-butyl radical, 2-ethylhexyl radical and 2-(2-ethoxyethoxy)ethyl radical; and B is a divalent radical obtained by eliminating two isocyanato radicals from hexamethylene diisocyanate or xylylene diisocyanate.

22. A moisture curable polyurethane composition comprising the β-amino-β-propiolactam derivative as claimed in claim 1 and a polyisocyanate and/or a polyurethane prepolymer having a terminal isocyanato radical.

23. A sealing or wall covering material of moisture curable polyurethane comprising the β-amino-β-propiolactam derivative as claimed in claim 1, the polyisocyanate and/or the polyurethane prepolymer having the terminal isocyanato radical, and a thixotropic agent.

24. The sealing or wall covering material of moisture curable polyurethane as claimed in claim 23 wherein the polyurethane prepolymer is a compound having the terminal isocyanato radical and being derived from the polyoxyalkylenepolyol and tolulene diisocyanate.

25. The sealing or wall covering material of moisture curable polyurethane as claimed in claim 23 wherein the thixotropic agent is a colloidal silica and/or a fatty acid amide wax.

26. A moisture curable polyurethane water proof material comprising the β-amino-β-propiolactam derivative as claimed in claim 1, the polyisocyanate and/or the polyurethane prepolymer having the terminal isocyanato radical, and a filler.

* * * * *

UNITED STATES PATENT AND TRADEMARK OFFICE
CERTIFICATE OF CORRECTION

PATENT NO. : 4,880,869

DATED : November 14, 1989

INVENTOR(S) : Aoki et al

It is certified that error appears in the above-identified patent and that said Letters Patent is hereby corrected as shown below:

In claim 4, line 1, before "amino" insert --β---.

In claim 6, line 2, delete "one of claim 1 to".

In claim 7, line 2, amend "propiolactar" to --propiolactam--; and line 3, delete "one of claim 1 to".

In claim 18, line 2, amend "I" to --1--.

In claim 20, line 4, amend "(v)" to -- (V) --; and line 9, amend "(polyethylene-oxy)" to -- (polyethyleneoxy) --.

In claim 21, line 1, amend "derivatives" to --derivative--; and line 4, amend "(v)" to -- (V) --.

In claim 24, line 5, amend "tolulene" to --tolylene--.

UNITED STATES PATENT AND TRADEMARK OFFICE
CERTIFICATE OF CORRECTION

PATENT NO. : 4,880,869

DATED : November 14, 1989

INVENTOR(S) : Aoki et al

It is certified that error appears in the above-identified patent and that said Letters Patent is hereby corrected as shown below:

In claim 24, line 5, amend "tolulene" to --tolylene--.

Signed and Sealed this

Twenty-fifth Day of December, 1990

Attest:

HARRY F. MANBECK, JR.

*Attesting Officer*    *Commissioner of Patents and Trademarks*